United States Patent
Otsubo et al.

(10) Patent No.: US 7,678,741 B2
(45) Date of Patent: *Mar. 16, 2010

(54) HERBICIDAL COMPOSITION

(75) Inventors: Toshiro Otsubo, Sanda (JP); Atsushi Watanabe, Toyonaka (JP); Aleksander Edward Karczewski, Berkeley, CA (US); Jane Qing Liu, Milpitas, CA (US)

(73) Assignees: Sumitomo Chemical Company, Limited, Tokyo (JP); Valent U.S.A. Corp., Walnut Creek, CA (US)

( * ) Notice: Subject to any disclaimer, the term of this patent is extended or adjusted under 35 U.S.C. 154(b) by 513 days.

This patent is subject to a terminal disclaimer.

(21) Appl. No.: 11/098,448

(22) Filed: Apr. 5, 2005

(65) Prior Publication Data

US 2006/0223710 A1    Oct. 5, 2006

(51) Int. Cl.
  *A01N 35/00*    (2006.01)
  *A01N 47/40*    (2006.01)
(52) U.S. Cl. .................................................. 504/343
(58) Field of Classification Search .................. 504/343
  See application file for complete search history.

(56) References Cited

U.S. PATENT DOCUMENTS

| | | | |
|---|---|---|---|
| 3,361,554 A * | 1/1968 | Weissenberger | ............ 504/192 |
| 4,626,276 A | 12/1986 | Luo | |
| 4,741,768 A | 5/1988 | Frazier et al. | |
| 4,946,681 A * | 8/1990 | Walter | ........................ 424/761 |
| 5,084,087 A * | 1/1992 | Hazen et al. | ................ 504/364 |
| 5,495,033 A | 2/1996 | Basu et al. | |
| 5,554,576 A | 9/1996 | Mookerjee et al. | |
| 5,624,883 A | 4/1997 | Basu et al. | |
| 5,815,942 A * | 10/1998 | Wu et al. | ........................ 34/78 |
| 6,780,885 B1 * | 8/2004 | Campbell et al. | ........... 514/424 |
| 2003/0104947 A1 | 6/2003 | Woznica et al. | |
| 2003/0125211 A1 | 7/2003 | Woznica et al. | |

OTHER PUBLICATIONS

G. Marc Loudon, Organic Chemistry, 1984 by Addion-Wesley Publishing Company, Inc. p. 899.*
U.S. Appl. No. 11/058,281, filed Feb. 16, 2005, Otsubo et al.
U.S. Appl. No. 11/058,246, filed Feb. 16, 2005, Otsubo et al.
U.S. Appl. No. 11/058,284, filed Feb. 16, 2005, Otsubo et al.
U.S. Appl. No. 11/071,204, filed Mar. 4, 2005, Otsubo et al.
U.S. Appl. No. 11/078,358, filed Mar. 14, 2005, Otsubo et al.

* cited by examiner

*Primary Examiner*—Alton N Pryor
(74) *Attorney, Agent, or Firm*—Sughrue Mion, PLLC

(57) ABSTRACT

A dehydration step provides a good storage stability to clethodium formulation. A herbicidal composition comprising clethodim as an active ingredient, wherein the content of water in the herbicidal composition is less than approximately 0.20% by weight provides a good storage stability of the clethodim in the composition.

13 Claims, No Drawings

HERBICIDAL COMPOSITION

FIELD OF THE INVENTION

The present invention relates to a herbicidal composition and a process for producing a herbicidal composition.

BACKGROUND ARTS

Some compositions containing a herbicidal cyclohexanedione compound are known in U.S. Pat. Nos. 4,626,276, 4,741,768, 5,084,087 and U.S. Pat. No. 5,554,576.

SUMMARY OF THE INVENTION

The present invention provides a herbicidal composition comprising clethodim as an active ingredient, wherein the content of water is less than approximately 0.20% by weight.

Further, the present invention provides a process for producing a herbicidal composition containing clethodim as an active ingredient which comprises a dehydration step.

According to the present invention, the herbicidal composition of the present invention or the herbicidal composition produced by the present process provides a good storage stability of the clethodim in the composition.

DISCLOSURE OF THE INVENTION

In the present invention, clethodim is an herbicidal ingredient, and the chemical name of clethodim is (±)-2-[(E)-1-[(E)-3-chloroallyloxyimino] propyl]-5-[2-(ethylthio)propyl]-3-hydroxyclclohex-2-enone of the formula:

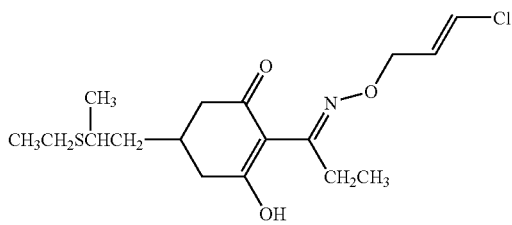

It can be obtained in the market, for example, it is provided by Valent U.S.A. Corporation or Arvesta Corporation.

The herbicidal composition of the present invention generally comprises i) clethodim, ii) an anionic surfactant, iii) a nonionic surfactant and iv) an aromatic hydrocarbon.

The content of the clethodim in the herbicidal composition is generally 5% to 40% by weight, preferably 10% to 30% by weight.

Sulfonate surfactant is generally used as the anionic surfactant. The sulfonate surfactant means an anionic surfactant having at least one sulfonic acid salt group in the molecule. Examples of the sulfonate surfactant include salts of alkylbenzene sulfonic acid (e.g., (C8-C15 alkyl)benzenesulfonate), salts of alkylnaphthalene sulfonic acid, salts of alkylsulfonic acid, salts of alkyl ether sulfonic acid, salts of fatty alcohol ether sulfonic acid and salts of polyoxyalkylene tristyrylphenyl ether sulfonic acid. Typical examples of the salt are calcium, sodium and potassium salts. Typical examples of the sulfonate are dodecylbenzenesulfonate, diisopropylnaphthalenesulfonate, diisobutylnaphthalenesulfonate, α-olefinsulfonate and dialkylsulfosuccinate.

Among them, calcium dodecylbenzenesulfonate, sodium dodecylbenzenesulfonate and potassium dodecylbenzenesulfonate are preferably used.

The content of the sulfonate surfactant in the herbicidal composition is generally 0.1% to 10% by weight, preferably 0.1% to 5% by weight.

Typical examples of the nonionic surfactant include polyoxyalkylene polyaryl ethers, polyoxyethylene plant oils, polyoxyalkylene fatty acid esters, polyoxyethylene sorbitan fatty acid esters, block copolymers of ethylene oxide and propylene oxide, polyoxyalkylene alkylphenyl ethers, polyoxyalkylene fatty alcohol ethers and polyoxyethylene alkanol amides.

The polyoxyalkylene polyaryl ether means a nonionic surfactant having two or more aromatic ring, wherein at least one aromatic ring has a polyoxyalkylene group, and an ether structure in the molecule. Typical examples of the polyoxyalkylene polyaryl ether include polyoxyalkylene styryl phenyl ether, polyoxyalkylene styryl phenylphenyl ether, polyoxyalkylene benzyl phenyl ether, polyoxyalkylene benzyl phenylphenyl ether and polyoxyalkylene bisphenyl ether. The polyoxyalkylene part is generally polyoxyethylene, polyoxypropylene or block copolymer of polyoxyethlene and polyoxypropylene. Typical examples are polyoxyalkylene tristyryl phenyl ether (e.g., polyoxyethylene tristyryl phenyl ether, polyoxyethylene polyoxypropylene tristyryl phenyl ether) and polyoxyalkylene distyryl phenyl ether (e.g., polyoxyethylene distyryl phenyl ether).

The HLB of the polyoxyalkylene polyaryl ether is preferably 12 to 15. HLB means Hydrophilic-Lipophilic Balance which is well known in the field of surfactant.

The polyoxyethylene plant oil is an addition product of ethylene oxide to plant oil. Typical example is polyoxyethylene castor oil.

The polyoxyalkylene fatty acid ester is a nonionic surfactant that is generally given by the formula:

wherein R is an alkyl or alkenyl group having 6 to 21 carbon atoms; AO is polyoxyethylene, polyoxypropylene or block copolymer of polyoxyethylene and polyoxypropylene; and n is 2 to 30.

The polyoxyalkylene fatty acid ester is obtained in the market or produced by known methods. For example, polyoxyethylene fatty acid esters can be produced by an addition of ethylene oxide to fatty acid or an esterification of fatty acid with polyethylene glycol.

The polyoxyalkylene fatty acid ester is preferably in the range of from 8 to 16 of HLB. Typical examples of the polyoxyalkylene fatty acid ester include polyoxyethylene monooleate, polyoxyethylene dioleate, polyoxyethylene monolaurate, polyoxyethylene dilaurate and polyoxyethylene monostearate.

The polyoxyethylene sorbitan fatty acid ester is an addition product of ethylene oxide to sorbitan fatty acid ester, wherein the fatty acid is generally saturated or unsaturated C8-C22 aliphatic acid. Examples of the polyoxyethylene sorbitan fatty acid ester include polyoxyethylene sorbitan monooleate, polyoxyethylene sorbitan monostearate, polyoxyethylene sorbitan monomyristate and polyoxyethylene sorbitan monotallate.

The block copolymer of ethylene oxide (EO) and propylene oxide (PO) is also called polyoxylethylene polyoxypropylene block copolymer. Examples of the block copolymer of ethylene oxide and propylene oxide are $(PO)_x$-$(EO)_y$, $(EO)_x$-

$(PO)_y$, $(PO)_x$-$(EO)_y$-$(PO)_z$, and $(EO)_x$-$(PO)_y$-$(EO)_z$. Among them, $(PO)_x$-$(EO)_y$-$(PO)_z$, namely

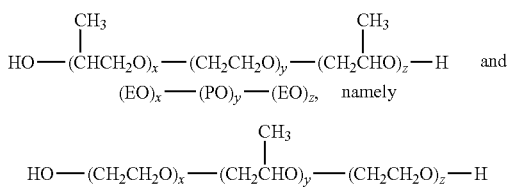

and $(EO)_x$—$(PO)_y$—$(EO)_z$, namely $$HO-(CH_2CH_2O)_x-(CH_2\overset{CH_3}{\underset{|}{C}}HO)_y-(CH_2CH_2O)_z-H$$

are preferably used.

The polyoxyalkylene alkylphenyl ether is also known as polyoxyalkylene alkyl phenol and it means a nonionic surfactant that is polyoxyalkylated alkylphenol. It is typically given by the formula: R—$C_6H_4$—O-$(AO)_n$H, wherein R is an alkyl, $(AO)_n$ is polyoxyethylene, polyoxypropylene or polyoxyethylene polyoxypropylene block copolymer and n is 2 to 50. Typical examples of the polyoxyalkylene alkylphenyl ether include polyoxyethylene nonylphenyl ether and polyoxyethylene octylphenyl ether.

The polyoxyalkylene fatty alcohol ether means a nonionic surfactant that is polyoxyalkylated fatty alcohol. It is also known as polyoxyalkylene alkyl ether. It is typically given by the formula: R—O-$(AO)_m$H, wherein R is a higher alkyl optionally containing one or more carbon-carbon double bonds therein, in other words, R may be alkenyl, $(AO)_m$ is polyoxyethylene, polyoxypropylene or polyoxyethylene polyoxypropylene block copolymer and m is 2 to 20. Typical examples of the polyoxyalkylene alkyl ether include polyoxyethylene lauryl ether, polyoxyethylene octyl ether, polyoxyethylene myristyl ether, polyoxyethylene stearyl ether and polyoxyethylene oleyl ether. It is prepared by addition of alkylene oxide (e.g., ethylene oxide, propylene oxide) of fatty alcohol, namely C10-C22 aliphatic alcohol.

The polyoxyalkylene alkanolamide is a polyoxyalkylenated fatty acid amide in general. It is typically given by the formula: $RCONH(AO)_nH$ or $RCON[(AO)_nH]_2$ wherein R is an alkyl group having 6 to 21 carbon atoms, $(AO)_n$ is polyoxyethylene, polyoxypropylene or polyoxyethylene polyoxypropylene block copolymer and n is 2 to 30. The RCONH $(AO)_nH$ type is preferably used. Examples of the polyoxyalkylene alkanolamide surfactant include polyoxyethylene lauramide, polyoxyethylene stearamide, polyoxyethylene cocamide, polyoxypropylene cocamide, polypropylene glycol 2-hydroxyethyl isostearamide and polypropylene glycol 2-hydroxyethyl cocamide.

The content of the nonionic surfactant in the herbicidal composition is generally 0.1% to 30% by weight, preferably 1% to 20% by weight.

Examples of the aromatic hydrocarbon include xylene, phenylxylylethane, Hisol SAS-296 (a mixture of 1-phenyl-1-xylylethane and 1-phenyl-1-ethylphenylethane, commercial name of Nippon Petroleum Company), Cactus Solvent HP-DMN (containing 80% of dimethylnaphthalene, commercial name of Nikko Petrochemical Company), Cactus Solvent P-100 (alkylbenzene having 9 to 10 of carbon number, commercial name of Nikko Petrochemical Company), Aromatic 150 (aromatic hydrocarbon, commercial name of ExxonMobil Chemical) and Aromatic 200 (aromatic hydrocarbon, commercial name of ExxonMobil Chemical).

The content of the aromatic hydrocarbon in the herbicidal composition of the present invention is generally 10% to 89.8% by weight.

Further, the herbicidal composition optionally comprises the other solvent, auxiliaries such as esters of fatty acid, antioxidant, fungicide, perfume, dyestuff, and so on.

The esters of fatty acid generally can work as enhancer of bioefficacy. The formula of esters of fatty acid is RCOOR'; wherein R is an alkyl group having 7 to 21 carbon atoms or an alkenyl group having 7 to 21 carbon atoms, and R' is an alkyl group having 1 to 8 carbon atoms. Examples of the group given by the formula RCO include palmitoyl, myristoyl, stearoyl, lauroyl and oleoyl. Examples of R' are methyl, ethyl, isopropyl, butyl, isobutyl and octyl. Typical examples of the esters of fatty acid are methyl oleate, methyl palmitate, methyl laurate, isopropyl myristate, isopropyl palmitate, octyl laurate, octyl palmitate and butyl stearate.

When the ester of fatty acid is used, the content of the ester of fatty acid in the herbicidal composition is generally 0.1% to 79.8% by weight, preferably 10% to 50% by weight. In addition, when the ester of fatty acid is used, the content of the aromatic hydrocarbon in the herbicidal composition of the present invention is preferably 10% to 60% by weight.

Preferably, propyl gallate is used for antioxidant; the content of the propyl gallate in the herbicidal composition is generally 0.01% to 10% by weight, preferably 0.1% to 3% by weight.

The present invention also provides a process for producing a herbicidal composition containing clethodim as an active ingredient which comprises a dehydration step. The herbicidal composition obtained by the process has a good storage stability of clethodim in the composition and the water content is generally less than approximately 0.20% by weight.

The process of the present invention is described in detail below.

The dehydration step can be applied to a mixture or a raw material and performed, for example, by bubbling dry gas such as air and nitrogen through liquid; by making the liquid contact with a water absorbable material such as porous crystalline zeolite (such as Molecular sieve 3A, Molecular sieve 4A, Molecular sieve 5A), anhydrous sodium sulfate, anhydrous calcium sulfate, anhydrous magnesium sulfate, calcium chloride and calcium oxide; or by azeotropic distillation using toluene, xylene, benzene, ethylbenzene and so on. The dry gas can be prepared by making a gas (e.g., nitrogen, compressed air) pass through a desiccant such as calcium chloride, silica and so on. Dry nitrogen can be available from the cylinder on the market as it is.

Namely, typical procedure is mixing clethodim, an anionic surfactant, a nonionic surfactant, an aromatic hydrocarbon and optionally the other solvent, auxiliaries and so on, and then bubbling dry gas through the mixture or making the mixture contact with a water absorbable material. Another typical procedure is mixing clethodim, an anionic surfactant, a nonionic surfactant, an aromatic hydrocarbon and optionally the other solvent, auxiliaries and so on, after bubbling dry gas through at least one raw material or making at least one raw material contact with a water absorbable material. The raw material to which the dehydration step is applied is generally the nonionic surfactant, or both of the nonionic surfactant and the solvent including the aromatic hydrocarbon.

The herbicidal composition of the present invention is utilized as an emulsifiable concentrate in general, namely it is diluted with water to give an emulsion and applied to weeds, especially graminaceous weeds such as *Agropyron tsukushiense*, barnyardgrass (*Echinochloa crus-galli*), green foxtail (*Setaria viridis*), giant foxtail (*Setaria faberi*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*) and bermudagrass (*Cynodon dactylon*) in broad-leaf crop (e.g. soybean, cotton, sugarbeet, peanut) fields. The application dosage is generally 10 g to 1000 g per hectare in the amount of clethodim, although it may vary with the kinds of objective weeds, weather conditions and so on. The dilution of the herbicidal composition can also be used for aerial application by helicopter, plane or radio-controlled helicopter. The herbicidal composition of the present invention may be diluted with water containing a spreading agent. Examples of the spreading agent include Agridex (commercial name of Helena Chemical Corporation), Dynamic (commercial name of Helena Chemical Corporation), Induce (commercial name of Helena Chemical Corporation) and Silwet L-77 (manufactured by Nihon Unicar).

EXAMPLES

Hereinafter, the present invention is explained in more detail referring to examples, but the present invention should not be limited to the following examples.

Example 1

A mixture was obtained by thoroughly mixing 21.5 wt % of clethodim (purity: 93%), 1.7 wt % of calcium dodecylbenzenesulfonate (60% calcium dodecylbenzenesulfonate in 2-ethylhexanol, Agnique ABS 60C supplied by Cognis), 2.0 wt % of polyoxyethylene polyoxypropylene tristyrylphenyl ether (HLB 13.5, Soprophor 796P supplied by Rhodia), 4.0 wt % of polyoxyethylene castor oil (HLB 13), 4.0 wt % of polyoxyethylene castor oil (HLB 10.8), 40.0 wt % of methyl oleate (Agnique ME 181-U supplied by Cognis) and 26.8 wt % of Aromatic 150 (aromatic hydrocarbon, commercial name of ExxonMobil Chemical). The content of water in the mixture was 0.23 wt %. (Reference composition 1)

About 150 ml of Reference composition 1 was charged into a 300-ml flask and about 40 ml/sec of dry nitrogen was bubbled for 2 hours. The content of water in the mixture was made to 0.01 wt %. (Composition 1)

Example 2

A mixture was obtained by thoroughly mixing 21.5 wt % of clethodim (purity: 93%), 1.7 wt % of calcium dodecylbenzenesulfonate (60% calcium dodecylbenzenesulfonate in 2-ethylhexanol, Agnique ABS 60C supplied by Cognis), 2.0 wt % of polyoxyethylene polyoxypropylene tristyrylphenyl ether (HLB 13.5, Soprophor 796P supplied by Rhodia), 11.0 wt % of polyoxyethylene castor oil (HLB 10.8), 40.0 wt % of butyl stearate and 23.8 wt % of Aromatic 150 (aromatic hydrocarbon, commercial name of ExxonMobil Chemical). The content of water in the mixture was made to 0.33 wt %. (Reference composition 2)

About 150 ml of Reference composition 2 was charged into a 300-ml flask and about 40 ml/sec of dry nitrogen was bubbled for 3 hours. The content of water in the mixture was made to 0.02 wt %. (Composition 2-1)

About 30 ml of Reference composition 2 was charged into a bottle with lid and about 15 g of Molecular sieve 3A was added and left for 3 hours. The content of water in the mixture was made to 0.07 wt %. (Composition 2-2)

Example 3

A mixture was obtained by thoroughly mixing 21.5 wt % of clethodim (purity: 93%), 1.7 wt % of calcium dodecylbenzenesulfonate (60% calcium dodecylbenzenesulfonate in 2-ethylhexanol, Agnique ABS 60C supplied by Cognis), 2.0 wt % of polyoxyethylene polyoxypropylene tristyrylphenyl ether (HLB 13.5, Soprophor 796P supplied by Rhodia), 6.0 wt % of polyoxyethylene castor oil (HLB 13), 6.0 wt % of polyoxyethylene castor oil (HLB 10.8) and 64.8 wt % of Aromatic 150 (aromatic hydrocarbon, commercial name of ExxonMobil Chemical). The content of water in the mixture was made to 0.32 wt %. (Reference composition 3)

About 150 ml of Reference composition 3 was charged into a 300 ml-flask and about 40 ml/sec of dry nitrogen was bubbled for 3 hours. The content of water in the mixture was made to 0.03 wt %. (Composition 3)

Example 4

A content of water in a polyoxyethylene polyoxypropylene tristyrylphenyl ether (HLB 13.5) was measured and the value was 0.14 wt %. Ten grams (10 g) of Molecular sieve 3A were added to 25 ml of the polyoxyethylene polyoxypropylene tristyrylphenyl ether and kept for 15 hours. The content of water was made to 0.04 wt %.

A content of water in calcium dodecylbenzenesulfonate (60% calcium dodecylbenzenesulfonate in 2-ethylhexanol, Agnique ABS 60C supplied by Cognis) was measured and the value was 0.68 wt %. Ten grams (10 g) of Molecular sieve 3A were added to 25 ml of calcium dodecylbenzenesulfonate and kept for 15 hours. The content of water was made to 0.04 wt %.

The raw materials obtained above can provide a herbicidal composition of the present invention.

Test Example

The herbicidal compositions listed in the following table were kept in 60° C. oven for 7 days, and the contents of clethodim were measured.

| Sample | Clethodim content (wt %) | | Decomposition ratio (wt %) |
| --- | --- | --- | --- |
| | Initial | After 7 days | |
| Reference Composition 1 | 20.1 | 17.6 | 12.4 |
| Composition 1 | 20.2 | 19.2 | 5.0 |
| Reference Composition 2 | 20.1 | 17.6 | 12.4 |
| Composition 2-1 | 20.3 | 19.1 | 5.9 |
| Composition 2-2 | 20.2 | 18.7 | 7.4 |
| Reference Composition 3 | 20.0 | 18.0 | 10.0 |
| Composition 3 | 20.4 | 19.3 | 5.4 |

As given by the table, the storage stability of clethodim was improved by the dehydration step.

We claim:

1. A herbicidal composition comprising clethodim as an active ingredient, wherein the content of water in the herbicidal composition is 0.01% by weight to less than 0.20% by weight.

2. The herbicidal composition according to claim 1, which comprises clethodim, an anionic surfactant, a nonionic surfactant and an aromatic hydrocarbon.

3. The herbicidal composition according to claim 2, which comprises 10 to 30% by weight of clethodim, 0.1 to 5% by weight of an anionic surfactant, 0.1 to 20% by weight of a nonionic surfactant and 10 to 89.8% by weight of an aromatic hydrocarbon.

4. A process for producing a herbicidal composition containing clethodim as an active ingredient which comprises dehydrating the clethodim composition.

5. The process according to claim 4, wherein the content of water in the final herbicidal composition is 0.01% by weight to less than 0.20% by weight.

6. The process according to claim 4, wherein the herbicidal composition comprises clethodim, an anionic surfactant, a nonionic surfactant and an aromatic hydrocarbon.

7. The process according to claim 4, wherein the final herbicidal composition comprises 10 to 30% by weight of clethodim, 0.1 to 5% by weight of an anionic surfactant, 0.1 to 20% by weight of a nonionic surfactant and 0.1 to 89.8% by weight of an aromatic hydrocarbon.

8. The process according to claim 4, wherein the dehydration step comprises bubbling of dry gas.

9. The process according to claim 8, wherein the dry gas is nitrogen.

10. The process according to claim 4, wherein the dehydration step comprises contacting with a water absorbable material.

11. The process according to claim 10, wherein the water absorbable material is at least one selected from the group consisting of Molecular sieve 3A, Molecular sieve 4A, Molecular sieve 5A and anhydrous sodium sulfate.

12. The process according to claim 4, wherein the dehydration step comprises azeotropic distillation.

13. The process according to claim 12, wherein the azeotropic distillation is an azeotropic distillation with toluene, xylene, benzene or ethylbenzene.

* * * * *